United States Patent
Mittendorf et al.

(10) Patent No.: US 10,844,396 B2
(45) Date of Patent: Nov. 24, 2020

(54) NUCLEIC ACID CONSTRUCT FOR CONFERRING HERBICIDE TOLERANCE IN PLANTS

(71) Applicants: SYNGENTA PARTICIPATIONS AG, Basel (CH); SYNGENTA CROP PROTECTION, LLC, Research Triangle Park, NC (US)

(72) Inventors: Volker Mittendorf, Research Triangle Park, NC (US); John Hipskind, Research Triangle Park, NC (US); Kasi Azhakanandam, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/558,298

(22) PCT Filed: Feb. 18, 2016

(86) PCT No.: PCT/US2016/018432
§ 371 (c)(1),
(2) Date: Sep. 14, 2017

(87) PCT Pub. No.: WO2016/153645
PCT Pub. Date: Sep. 29, 2016

(65) Prior Publication Data
US 2018/0057836 A1    Mar. 1, 2018

Related U.S. Application Data

(60) Provisional application No. 62/137,177, filed on Mar. 23, 2015.

(51) Int. Cl.
*C12N 15/82*    (2006.01)

(52) U.S. Cl.
CPC ..... *C12N 15/8277* (2013.01); *C12N 15/8275* (2013.01)

(58) Field of Classification Search
None
See application file for complete search history.

(56) References Cited

U.S. PATENT DOCUMENTS 10,448,588 B2 *  10/2019  Chintamanani .... C12N 15/8218

FOREIGN PATENT DOCUMENTS

| WO | 2010144385 A1 | 12/2010 |
| WO | 2012088342 A1 | 6/2012 |

OTHER PUBLICATIONS

International Search Report for International Application No. PCT/US16/18432 dated May 20, 2016.

\* cited by examiner

*Primary Examiner* — Mykola V. Kovalenko
(74) *Attorney, Agent, or Firm* — R. Kody Jones

(57) ABSTRACT

The present invention is drawn to a nucleic acid sequence which confers expression of a phosphinothricin acetyltransferase and a 5-enolpyruvyl-3-phosphoshikimic acid synthase when introduced into a cell. These proteins may confer herbicide tolerance.

20 Claims, 1 Drawing Sheet
Specification includes a Sequence Listing.

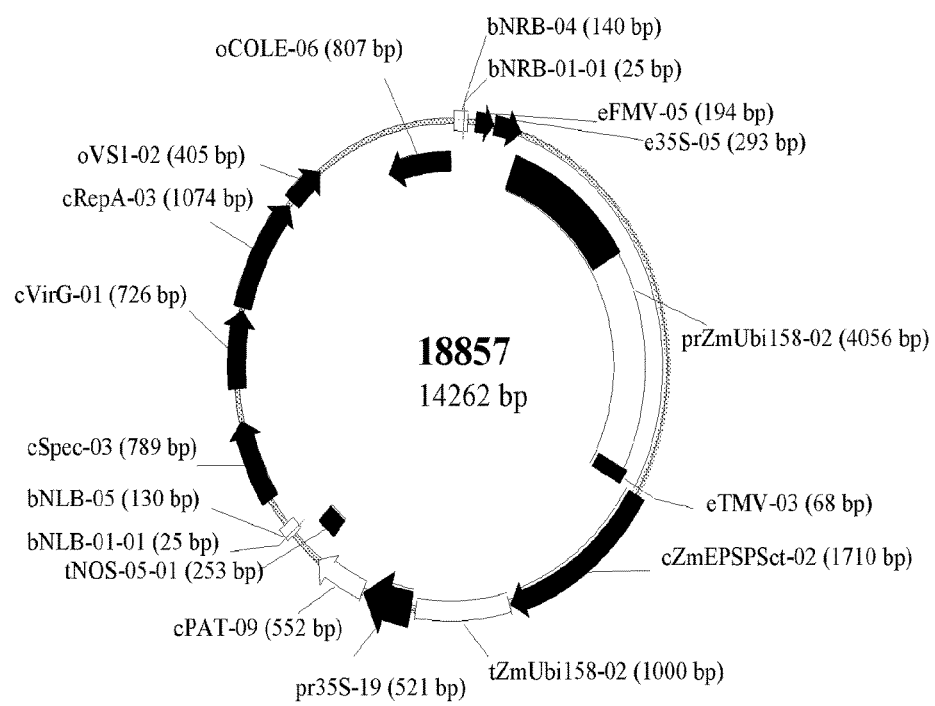

SEQUENCE LISTING

```
<160> NUMBER OF SEQ ID NOS: 2

<210> SEQ ID NO 1
<211> LENGTH: 8676
<212> TYPE: DNA
<213> ORGANISM: Artificial Sequence
<220> FEATURE:
<223> OTHER INFORMATION: Source organisms include Figwort Mosaic Virus,
      Cauliflower Mosaic Virus, Zea mays, Streptomyces
      viridochromogenes, and Agrobacterium tumefaciens

<400> SEQUENCE: 1
agctgcttgt ggggaccaga caaaaaagga atggtgcaga attgttaggc gcacctacca      60
aaagcatctt tgcctttatt gcaaagataa agcagattcc tctagtacaa gtggggaaca     120
aaataacgtg gaaaagagct gtcctgacag cccactcact attgcgtttg acgaacgcag     180
tgacgaccac aaaactcgag acttttcaac aaagggtaat atccggaaac ctcctcggat     240
tccattgccc agctatctgt cactttattg tgaagatagt ggaaaaggaa ggtggctcct     300
acaaatgcca tcattgcgat aaaggaaagg ctatcgttga agatgcctct gccgacagtg     360
gtcccaaaga tggaccccca cccacgagga gcatcgtgga aaaagaagac gttccaacca     420
cgtcttcaaa gcaagtggat tgatgtgata tctccactga cgtaagggat gacgaacaat     480
cccactatcc ttctgccgga ccctggaaaa ccaaaacaac gaataagcaa actgcaggaa     540
```

```
aagtatgcag tggaaaccaa cccagattcg gacgatagga aagtatcaag tgaatgattt    600
gccaggaaaa ggagaggggt aaaaaggggc gaagatttag aagatctaaa gcacaagaac    660
cagagattag attgaacaat agggaacttg gagcatcctt tttttcttca gggaaaaact    720
gaaaatccaa accatgttga gcaaaaccga gtgggattgg aaaccaaaaa acccgagata    780
aagaaactcg agaaaaagca tgaaatcgaa accaacttca gtaaaacaaa aggaggacag    840
aaaagaaagt cggaaggtat aaagaataca ttaacattca gtgaaacagc atgctgtctt    900 cttcttttt tatgcacaac agagcataca tatataccct cccaggctga ggacttggcg    960
gaggagagcc gcggagaggt tggcggtgca gacggtctgg acgggcccga agacggagac   1020
gaacagcggg cccttcctgc ccaggcacca cgcttggaac gccaagcacg cgccaaccgc   1080
ggccccgccg aggacgacga tccccgcgac aagcgtggcg tcgatcctgg gcgaccccaa   1140
gccgaggaac ctcccttcca ggacgagccg caggacggcg gtgagagagg cacccgtcgc   1200
ggaggtggcg cagcacaagg tgagcagcgc ggggaaggcg gcgagcgtgg cggcctgcag   1260
gacggtgacg agcgcgaaga cggtgacgcc ggcgacgagg cagcagcagc cgaggatcca   1320
gtcgtaggag aagccggac caaaccgggc aatgcaacct gcagatgcac tagacggagg   1380
aaacgaggag gaggagaaaa cagagcaaga gcaggcggag agaagataga gcaaaacacg   1440
agtgaggcac agcgtaagca ctcggtagaa gtctccagag gcgaggtgcg cacaggagaa   1500
cagatgagta aagtcagcca aggatccacg atccaacggc tacgaatttt tggagtgacg   1560
tggataggct caaaggcgcc atttccatcc ggctttatag tattttaaaa aaattcattt   1620
tcctccctct agtgtgtgcg gaggcgtgag cccgtttaac ggcgttgaga agtctaacgg   1680
acaccaacca caaccaggaa ccagcgccgg ccgcgccgcc gagtgaagca gactgcatac   1740 ggcacgcgc ggcatctctc tggctgcctc tcgagagttc cgcccccacc ttcccgcggt   1800
agcgtggtgg tttcgctttc cgctgtcggc atccggaagt tgcgtggcag agtggacgga   1860
gacgaggccg ggtcctccag ctcctctcaa acgtcacggc accggcatcc ggcagccagc   1920
gcggtccttc ccaaccactc gttcccaacc catccccctt cctcgcccgc cgtcataaat   1980
agccagcccc atcccagct tctttcccca acctcatctt ctctccttt gctctgaacg   2040 cacacaccgc ccggtctccg atctccgatc cccgatcccc tcgtcgatcc taggtacggc   2100
gaccatcctc cccccccccc cccccctct ctctctgcct tctctagatc ggcgatccga   2160
tccatgctta cttggttagg gcctgctaac tatgttcatg tttgcgttag atccgtgcat   2220
ggacgcgatc tgtacacacc agacgcgttc tgattgctag ctaactcgcc agtacctggg   2280
aatcctggga tggctgtagc cggccccgca cgcagacggg accgatttca tgattctcta   2340 ttttttct tgtttcgttg cctagggttt cgttcgatcg atccgcgtta ttctttattt   2400
ccatatattc tggtacgatg ttgatacggt tcgaccgtgc tgcttacgtt ctgtgcgctt   2460
gtttgccggg tcattttttac cttgccttt ttgtatggtt tggttgtggc gatgtggtct   2520
ggtcgggctg tcgttctaga tcggagtaga gtgctgtttc aaactgtcta gcggatctat   2580
tagatttgga tctgcatgtg tgacatatat cttcgtagtt aagatgatgc atctgtatgt   2640
gtgacatgcg gatctattag atttggatct gtatgtgtga catatatctt cgtagttgag   2700
atgatgcatc tgtatgtgtg acatatatct tcgtagttaa gattatgcat ggaaatatca   2760
atcctttaga taaggacggg tatacttgtt gctgtgggtt ttactggtac ttcgatagat   2820
gcatatacat gatctaacat gcttagatac atgaagtaac atgctgctac ggtttaataa   2880
ttcttgagtt gatttttact ggtacttaga tagatgtata tacatgctta gatacatgaa   2940
```

```
gtaacatgct cctacagttc ctttaatcat tattgagtac ctatatattc taataaatca    3000
gtatgtttta aattattttg attttactgg tacttagata gatgtatata tacatgctca    3060
aacatgctta gatacatgaa gtaacatgct gctacggttt agtcattatt gagtgcctat    3120
atattctaat aaatcagtat gttttaaatt attttgattt tactggtact tagatagatg    3180
tatatataca tgctcaaaca tgcttagata catgaagtaa tatgctacta cggtttaatt    3240
gttcttgagt acctatatat tctaataaat cagtatgttt taaattattt cgattttact    3300
ggtacttaga tagatgtata tatacatgct tagatacatg aagtaacatg ctactacggt    3360
ttaattgttc ttgaatacct atatattcta ataaatcagt atgttttaaa ttatttcgat    3420
tttactggta cttagataga tgtatatata catgctcgaa catgcttaga tacatgaagt    3480
aacatgctac atatatatta taataaatca gtatgtctta aattattttg attttactgg    3540
tacttagata gatgtatata catgctcaaa catgcttaga tacatgaagt aacatgctac    3600
tacggtttaa tcattattga gtacctatat attctaataa atcagtatgt tttcaattgt    3660
tttgatttta ctggtactta gatatatgta tatacatgc tcgaacatg cttagatacg    3720 tgaagtaaca tgctactatg gttaattgtt cttgagtacc tatatattct aataaatcag    3780
tatgttttaa attatttcga ttttactggt acttagatag atgtatatat acatgctcga    3840
acatgcttag atacatgaag taacatgcta ctacggttta atcgttcttg agtacctata    3900
tattctaata aatcagtatg tcttaaatta tcttgatttt actggtactt agatagatgt    3960
atatacatgc ttagatacat gaagtaacat gctactatga tttaatcgtt cttgagtacc    4020
tatatattct aataaatcag tatgttttta attattttga ttttactggt acttagatag    4080
atgtatatat acatgctcga acatgcttag atacatgaag taacatgcta ctacggttta    4140
atcattcttg agtacctata tattctaata aatcagtatg ttttaatta tttgatatt    4200 actggtactt aacatgttta gatacatcat atagcatgca catgctgcta ctgtttaatc    4260
attcgtgaat acctatatat tctaatatat cagtatgtct tctaattatt atgattttga    4320
tgtacttgta tggtggcata tgctgcagct atgtgtagat tttgaatacc cagtgtgatg    4380
agcatgcatg gcgccttcat agttcatatg ctgtttattt cctttgagac tgttcttttt    4440
tgttgatagt caccctgttg tttggtgatt cttatgcaga tccagatctt cgtattttta    4500
caacaattac caacaacaac aaacaacaaa caacattaca attactattt acataaacca    4560
tggcttcgat ctcctcctca gtcgcgaccg ttagcaggac cgcccctgct caggccaaca    4620
tggtggctcc gttcaccggc cttaagtcca acgccgcctt ccccaccacc aagaaggcta    4680
acgacttctc caccctgccc agcaacggtg aaagagttca gtgtatgcag gtgtggccgg    4740
cctacggcaa caagaagttc gagacgctgt cgtacctgcc gccgctgtct atggcgccca    4800
ccgtgatgat ggcctcgtcg gccaccgccg tcgctccgtt ccaggggctc aagtccaccg    4860
ccagcctccc cgtcgcccgc cgctcctcca gaagcctcgg caacgtcagc aacgcggaa    4920 gaatccggtg catggccggt gccgaggaga tcgtgctgca gccgatcaag gagatcagcg    4980
gcaccgtgaa gctgcggggc agcaagagcc tgagcaaccg catcctgctg ctggccgccc    5040
tgagcgaggg caccaccgtg gtggacaacc tgctgaacag cgaggacgtg cactacatgc    5100
tgggcgccct gaggaccctg ggcctgagcg tggaggccga caaggccgcc aagagggccg    5160
tggtggtggg ctgcggcggc aagttcccgg tggaggacgc caaggaggag gtgcagctgt    5220
tcctgggcaa cgccggcatc gccatgagga gcctgaccgc cgccgtgacc gccgccggcg    5280
```

```
gcaacgccac ctacgtgctg acggcgtgc cgaggatgag ggagaggccg atcggcgacc      5340
tggtggtggg cctgaagcag ctgggcgccg acgtggactg cttcctgggc accgactgcc      5400
cgccggtgag ggtgaacggc atcggcggcc tgccgggcgg caaggtgaag ctgagcggca      5460
gcatcagcag ccagtacctg agcgccctgc tgatggccgc cccgctggcc ctgggcgacg      5520
tggagatcga gatcatcgac aagctgatca gcatcccgta cgtggagatg accctgaggc      5580
tgatggagag gttcggcgtg aaggccgagc acagcgacag ctgggacagg ttctacatca      5640
agggcggcca gaagtacaag agcccgaaga acgcctacgt ggagggcgac gccagcagcg      5700
ccagctactt cctggccggc gccgccatca ccggcggcac cgtgaccgtg gagggctgcg      5760
gcaccaccag cctgcagggc gacgtgaagt cgccgaggt gctggagatg atgggcgcca      5820
aggtgacctg gaccgagacc agcgtgaccg tgaccggccc gccgagggag ccgttcggca      5880
ggaagcacct gaaggccatc gacgtgaaca tgaacaagat gccggacgtg gccatgaccc      5940
tggccgtggt ggccctgttc gccgacggcc cgaccgccat cagggacgtg gccagctgga      6000
gggtgaagga gaccgagagg atggtggcca tcaggaccga gctgaccaag ctgggcgcca      6060
gcgtggagga gggcccggac tactgcatca tcaccccgcc ggagaagctg aacgtgaccg      6120
ccatcgacac ctacgacgac cacaggatgg cgatggcctt cagcctggcc gcctgcgccg      6180
aggtgccggt gaccatcaga gacccgggct gcaccaggaa gaccttcccg gactacttcg      6240
acgtgctgag caccttcgtg aagaactaaa gagctcgcca aggttcaatt aagctgctgc      6300
tgtacctggg tatctgcgtc gtctggtgcc ctctggtgta cctctatatg gatgtcgtcg      6360
tctaataaac atctgtggtt tgtgtgtcat gaatcgtggt tgtggcttcg ttggtttaat      6420
ggacctgttg tgtcctctgt gttgtaccca aaactcttct gcagcagtat ggcttgaatc      6480
cttatgaagt ttgatatttg aacttaaaag tctgctcatt atgttttttt ctggttatat      6540
ctcctaatta actgcctggg atcaaatttg attcgctggt gtttattgga cccctcccag      6600
gttcttgctt tctaccgttt cttgctgaat gttaacttga ttctgtcagg ctcagtttcc      6660
cactatggct tacagcttaa cgtgtttggt ttgttgaatg ttaacttggt tttgtcaagc      6720
tcagtttttt actctggctt acagcataac atgtttgact tttggttttg ctgctttgtt      6780
attgggttct gggtagttct tgatgaatcc aaaagatcat gtgcacagcc atattatcta      6840
tttaagcgat ccaggttatt actatgaaag gatgccttct agctaaggag tagttaggtt      6900
ttttcttcaa ggttaaattt tctcgatgct ctagtgttcc tgtgaccata atcataataa      6960
ttcctttgaa agctctatgg tccctggaag cagggcatac aatgcaagac agcaacttga      7020
tcacatcaac tgaagtatac agggttctct taactcttgg tgacttcggt ttaatggacc      7080
ggttgtactc gtgttctatc cgtaaccgtt gtgatgtctt gtgtgtttgg ttgcgggata      7140
gctgggacca cgacgtttcc gtctaattct gatggatagc tatagacggc actgagatgg      7200
ttatattata acctctgatc ctgaactcta cgagatcgtc tcatccgtca ttgccaccaa      7260
atacaccatt aaattacgga cccgatttaa ataatattcg gaccgctagt gcatgcactg      7320
actaattagc taaagtcaaa gattcaaata gaggacctaa cagaactcgc cgtaaagact      7380
ggcgaacagt tcatacagag tctcttacga ctcaatgaca agaagaaaat cttcgtcaac      7440
ttggtggagc acgacacgct agtctactcc aaaaatatca aagatacagt ctcagaagac      7500
caaagggcaa ttgagacttt tcaacaaagg gtaatatccg gaaacctcct cggattccat      7560
tgcccagcta tctgtcactt aattgtgaag atagtggaaa aggaaggtgg ctcctacaaa      7620
tgccatcatt gcgataaagg aaaggccatc gttgaagatg cctctgccga cagtggtccc      7680
```

```
aaagatggac ccccacccac gaggagcatc gtggtaaaag aagacgttcc aaccacgtct    7740
tcaaagcaag tggattgatg tgatatctcc actgacgtaa gggatgacgc acaatcccac    7800
tatccttcgc aagacccttc ctctatataa ggaagttcat ttcatttgga gaggataatt    7860
atccaccatg tctccggaga ggagaccagt tgagattagg ccagctacag cagctgatat    7920
ggccgcggtt tgtgatatcg ttaaccatta cattgagacg tctacagtga actttaggac    7980
agagccacaa acaccacaag agtggattga tgatctagag aggttgcaag atagatcccc    8040
ttggttggtt gctgaggttg agggtgttgt ggctggtatt gcttacgctg ggccctggaa    8100
ggctaggaac gcttacgatt ggacagttga gagtactgtt tacgtgtcac ataggcatca    8160
aaggttgggc ctaggctcca cattgtacac acatttgctt aagtctatgg aggcgcaagg    8220
ttttaagtca gtggttgctg ttataggcct tccaaacgat ccatctgtta ggttgcatga    8280
ggctctagga tacacagcgc ggggtacact gcgcgcagct ggatacaagc atggtggatg    8340
gcatgatgtt ggttttttggc aaagggattt tgagttgcca gctcctccaa ggccagtgag    8400
gccagttacc cagatctgac taagatcgtt caaacatttg gcaataaagt ttcttaagat    8460
tgaatcctgt tgccggtctt gcgatgatta tcatataatt tctgttgaat tacgttaagc    8520
atgtaataat taacatgtaa tgcatgacgt tatttatgag atgggttttt atgattagag    8580
tcccgcaatt atacatttaa tacgcgatag aaaacaaaat atagcgcgca aactaggata    8640
aattatcgcg cgcggtgtca tctatgttac tagatc                             8676

<210> SEQ ID NO 2
<211> LENGTH: 14262
<212> TYPE: DNA
<213> ORGANISM: Artificial Sequence
<220> FEATURE:
<223> OTHER INFORMATION: Source organisms include Figwort Mosaic Virus,
      Cauliflower Mosaic Virus, Zea mays, Streptomyces
      viridochromogenes, Agrobacterium tumefaciens, Pseudomonas spp, and
      Escherichia coli

<400> SEQUENCE: 2
attcctgtgg ttggcatgca catacaaatg gacgaacgga taaaccttt cacgcccttt     60 taaatatccg attattctaa taaacgctct tttctcttag gtttaccccgc caatatatcc    120 tgtcaaacac tgatagttta aactggcact agcctaacgg tgttgactaa ctaggccgct    180
tccctaatta gctaaccatg gcccgggact gaggcgcgcc gggacccagc tgcttgtggg    240
gaccagacaa aaaaggaatg gtgcagaatt gttaggcgca cctaccaaaa gcatctttgc    300
ctttattgca aagataaagc agattcctct agtacaagtg gggaacaaaa taacgtggaa    360
aagagctgtc ctgacagccc actcactatt gcgtttgacg aacgcagtga cgaccacaaa    420
actcgagact tttcaacaaa gggtaatatc cggaaacctc ctcggattcc attgcccagc    480
tatctgtcac tttattgtga agatagtgga aaggaaggt ggctcctaca aatgccatca    540
ttgcgataaa ggaaaggcta tcgttgaaga tgcctctgcc gacagtggtc ccaaagatgg    600
acccccaccc acgaggagca tcgtggaaaa agaagacgtt ccaaccacgt cttcaaagca    660
agtggattga tgtgatatct ccactgacgt aagggatgac gaacaatccc actatccttc    720
tgccggaccc tggaaaacca aaacaacgaa taagcaaact gcaggaaaag tatgcagtgg    780
aaaccaaccc agattcggac gataggaaag tatcaagtga atgatttgcc aggaaaagga    840
gaggggtaaa aaggggcgaa gatttagaag atctaaagca caagaaccag agattagatt    900
gaacaatagg gaacttggag catccttttt ttcttcaggg aaaaactgaa aatccaaacc    960
```

```
atgttgagca aaaccgagtg ggattggaaa ccaaaaaacc cgagataaag aaactcgaga    1020
aaaagcatga aatcgaaacc aacttcagta aaacaaaagg aggacagaaa agaaagtcgg    1080
aaggtataaa gaatacatta acattcagtg aaacagcatg ctgtcttctt ctttttttat    1140
gcacaacaga gcatacatat ataccttccc aggctgagga cttggcggag agagccgcg     1200 gagaggttgg cggtgcagac ggtctggacg ggcccgaaga cggagacgaa cagcgggccc    1260
ttcctgccca ggcaccacgc ttggaacgcc aagcacgcgc caaccgcggc cccgccgagg    1320
acgacgatcc ccgcgacaag cgtggcgtcg atcctgggcg accccaagcc gaggaacctc    1380
ccttccagga cgagccgcag gacgcggtg agagaggcac ccgtcgcgga ggtggcgcag     1440
cacaaggtga gcagcgcggg gaaggcggcg agcgtggcgg cctgcaggac ggtgacgagc    1500
gcgaagacgt tgacgccggc gacgaggcag cagcagccga ggatccagtc gtaggaggaa    1560
gccggaccaa accgggcaat gcaacctgca gatgcactag acggaggaaa cgaggaggag    1620
gagaaaacag agcaagagca ggcggagaga agatagagca aaacgagt gaggcacagc      1680 gtaagcactc ggtagaagtc tccagaggcg aggtgcgcac aggagaacag atgagtaaag    1740
tcagccaagg atccacgatc caacggctac gaattttttgg agtgacgtgg ataggctcaa   1800
aggcgccatt tccatccggc tttatagtat tttaaaaaaa ttcattttcc tccctctagt    1860
gtgtgcggag gcgtgagccc gtttaacggc gttgagaagt ctaacggaca ccaaccacaa    1920
ccaggaacca gcgccggccg cgccgccgag tgaagcagac tgcatacggc acggcgcggc    1980
atctctctgg ctgcctctcg agagttccgc ccccaccttc ccgcggtagc gtggtggttt    2040
cgctttccgc tgtcggcatc cggaagttgc gtggcagagt ggacggagac gaggccgggt    2100
cctccagctc ctctcaaacg tcacggcacc ggcatccggc agccagcgcg gtccttccca    2160
accactcgtt cccaacccat cccccttcct cgcccgccgt cataaatagc cagccccatc    2220
cccagcttct ttccccaacc tcatcttctc tccttttgct ctgaacgcac acaccgcccg    2280
gtctccgatc tccgatcccc gatcccctcg tcgatcctag gtacggcgac catcctcccc    2340
cccccccccc cccctctctc tctgccttct ctagatcggc gatccgatcc atgcttactt    2400
ggttagggcc tgctaactat gttcatgttt gcgttagatc cgtgcatgga cgcgatctgt    2460
acacaccaga cgcgttctga ttgctagcta actcgccagt acctgggaat cctgggatgg    2520
ctgtagccgg ccccgcacgc agacgggacc gatttcatga ttctctattt ttttctttgt    2580
ttcgttgcct agggtttcgt tcgatcgatc cgcgttattc tttatttcca tatattctgg    2640
tacgatgtta atacggttcg accgtgctgc ttacgttctg tgcgcttgtt tgccgggtca    2700 ttttttacctt gccttttttg tatggtttgg ttgtggcgat gtggtctggt cgggctgtcg   2760
ttctagatcg gagtagagtg ctgtttcaaa ctgtctagcg gatctattag atttggatct    2820
gcatgtgtga catatatctt cgtagttaag atgatgcatc tgtatgtgtg acatgcggat    2880
ctattagatt tggatctgta tgtgtgacat atatcttcgt agttgagatg atgcatctgt    2940
atgtgtgaca tatatcttcg tagttaagat tatgcatgga aatatcaatc ctttagataa    3000
ggacgggtat acttgttgct gtgggttttta ctggtacttc gatagatgca tatacatgat   3060
ctaacatgct tagatacatg aagtaacatg ctgctacggt ttaataattc ttgagttgat    3120
ttttactggt acttagatag atgtatatac atgcttagat acatgaagta acatgctcct    3180
acagttcctt taatcattat tgagtaccta tatattctaa taaatcagta tgttttaaat    3240
tattttgatt ttactggtac ttagatagat gtatatatac atgctcaaac atgcttagat    3300
```

```
acatgaagta acatgctgct acggtttagt cattattgag tgcctatata ttctaataaa    3360
tcagtatgtt ttaaattatt ttgattttac tggtacttag atagatgtat atatacatgc    3420
tcaaacatgc ttagatacat gaagtaatat gctactacgg tttaattgtt cttgagtacc    3480
tatatattct aataaatcag tatgttttaa attatttcga ttttactggt acttagatag    3540
atgtatatat acatgcttag atacatgaag taacatgcta ctacggttta attgttcttg    3600
aatacctata tattctaata aatcagtatg ttttaaatta tttcgatttt actggtactt    3660
agatagatgt atatatacat gctcgaacat gcttagatac atgaagtaac atgctacata    3720
tatattataa taaatcagta tgtcttaaat tattttgatt ttactggtac ttagatagat    3780
gtatatacat gctcaaacat gcttagatac atgaagtaac atgctactac ggtttaatca    3840
ttattgagta cctatatatt ctaataaatc agtatgtttt caattgtttt gattttactg    3900
gtacttagat atatgtatat atacatgctc gaacatgctt agatacgtga agtaacatgc    3960
tactatggtt aattgttctt gagtacctat atattctaat aaatcagtat gttttaaatt    4020
atttcgattt tactggtact tagatagatg tatatataca tgctcgaaca tgcttagata    4080
catgaagtaa catgctacta cggtttaatc gttcttgagt acctatatat tctaataaat    4140
cagtatgtct taaattatct tgattttact ggtacttaga tagatgtata tacatgctta    4200
gatacatgaa gtaacatgct actatgattt aatcgttctt gagtacctat atattctaat    4260
aaatcagtat gttttttaatt attttgattt tactggtact tagatagatg tatatataca    4320
tgctcgaaca tgcttagata catgaagtaa catgctacta cggtttaatc attcttgagt    4380
acctatatat tctaataaat cagtatgttt ttaattattt tgatattact ggtacttaac    4440
atgtttagat acatcatata gcatgcacat gctgctactg tttaatcatt cgtgaatacc    4500
tatatattct aatatatcag tatgtcttct aattattatg attttgatgt acttgtatgg    4560
tggcatatgc tgcagctatg tgtagatttt gaatacccag tgtgatgagc atgcatggcg    4620
ccttcatagt tcatatgctg tttatttcct ttgagactgt tcttttttgt tgatagtcac    4680
cctgttgttt ggtgattctt atgcagatcc agatcttcgt atttttacaa caattaccaa    4740
caacaacaaa caacaaacaa cattacaatt actatttaca taaaccatgg cttcgatctc    4800
ctcctcagtc gcgaccgtta gcaggaccgc ccctgctcag gccaacatgg tggctccgtt    4860
caccggcctt aagtccaacg ccgccttccc caccaccaag aaggctaacg acttctccac    4920
ccttcccagc aacggtggaa gagttcagtg tatgcaggtg tggccggcct acggcaacaa    4980
gaagttcgag acgctgtcgt acctgccgcc gctgtctatg gcgcccaccg tgatgatggc    5040
ctcgtcggcc accgccgtcg ctccgttcca ggggctcaag tccaccgcca gcctccccgt    5100
cgcccgccgc tcctccagaa gcctcggcaa cgtcagcaac ggcggaagaa tccggtgcat    5160
ggccggtgcc gaggagatcg tgctgcagcc gatcaaggag atcagcggca ccgtgaagct    5220
gccgggcagc aagagcctga gcaaccgcat cctgctgctg gccgccctga gcgagggcac    5280
caccgtggtg gacaacctgc tgaacagcga ggacgtgcac tacatgctgg gcgccctgag    5340
gaccctgggc ctgagcgtgg aggccgacaa ggccgccaag agggccgtgg tggtgggctg    5400
cggcggcaag ttcccggtgg aggacgccaa ggaggaggtg cagctgttcc tgggcaacgc    5460
cggcatcgcc atgaggagcc tgaccgccgc cgtgaccgcc gccggcggca acgccaccta    5520
cgtgctggac ggcgtgccga ggatgaggga gaggccgatc ggcgacctgg tggtgggcct    5580
gaagcagctg ggcgccgacg tggactgctt cctgggcacc gactgccgc cggtgagggt    5640
gaacggcatc ggcggcctgc cgggcggcaa ggtgaagctg agcggcagca tcagcagcca    5700
```

```
gtacctgagc gccctgctga tggccgcccc gctggccctg ggcgacgtgg agatcgagat   5760
catcgacaag ctgatcagca tcccgtacgt ggagatgacc ctgaggctga tggagaggtt   5820
cggcgtgaag gccgagcaca gcgacagctg ggacaggttc tacatcaagg cggccagaa   5880 gtacaagagc ccgaagaacg cctacgtgga gggcgacgcc agcagcgcca gctacttcct   5940
ggccggcgcc gccatcaccg gcggcaccgt gaccgtggag ggctgcggca ccaccagcct   6000
gcagggcgac gtgaagttcg ccgaggtgct ggagatgatg ggcgccaagg tgacctggac   6060
cgagaccagc gtgaccgtga ccggcccgcc gagggagccg ttcggcagga agcacctgaa   6120
ggccatcgac gtgaacatga acaagatgcc ggacgtggcc atgaccctgg ccgtggtggc   6180
cctgttcgcc gacggcccga ccgccatcag ggacgtggcc agctggaggg tgaaggagac   6240
cgagaggatg gtggccatca ggaccgagct gaccaagctg ggcgccagcg tggaggaggg   6300
cccggactac tgcatcatca ccccgccgga gaagctgaac gtgaccgcca tcgacaccta   6360
cgacgaccac aggatggcga tggccttcag cctggccgcc tgcgccgagg tgccggtgac   6420
catcagagac ccgggctgca ccaggaagac cttcccggac tacttcgacg tgctgagcac   6480
cttcgtgaag aactaaagag ctcgccaagg ttcaattaag ctgctgctgt acctgggtat   6540
ctgcgtcgtc tggtgccctc tggtgtacct ctatatggat gtcgtcgtct aataaacatc   6600
tgtggtttgt gtgtcatgaa tcgtggttgt ggcttcgttg gtttaatgga cctgttgtgt   6660
cctctgtgtt gtacccaaaa ctcttctgca gcagtatggc ttgaatcctt atgaagtttg   6720
atatttgaac ttaaaagtct gctcattatg ttttttttctg gttatatctc ctaattaact   6780
gcctgggatc aaatttgatt cgctggtgtt tattggaccc ctcccaggtt cttgctttct   6840
accgtttctt gctgaatgtt aacttgattc tgtcaggctc agtttcccac tatggcttac   6900
agcttaacgt gtttggtttg ttgaatgtta acttggtttt gtcaagctca gttttttact   6960
ctggcttaca gcataacatg tttgactttt ggttttgctg ctttgttatt gggttctggg   7020
tagttcttga tgaatccaaa agatcatgtg cacagccata ttatctattt aagcgatcca   7080
ggttattact atgaaaggat gccttctagc taaggagtag ttaggttttt tcttcaaggt   7140
taaattttct cgatgctcta gtgttcctgt gaccataatc ataataattc ctttgaaagc   7200
tctatggtcc ctggaagcag ggcatacaat gcaagacagc aacttgatca catcaactga   7260
agtatacagg gttctcttaa ctcttggtga cttcggttta atggaccggt tgtactcgtg   7320
ttctatccgt aaccgttgtg atgtcttgtg tgtttggttg cgggatagct gggaccacga   7380
cgtttccgtc taattctgat ggatagctat agacggcact gagatggtta tattataacc   7440
tctgatcctg aactctacga gatcgtctca tccgtcattg ccaccaaata caccattaaa   7500
ttacggaccc gatttaaata atattcggac cgctagtgca tgcactgact aattagctaa   7560
agtcaaagat tcaaatagag gacctaacag aactcgccgt aaagactggc gaacagttca   7620
tacagagtct cttacgactc aatgacaaga agaaaatctt cgtcaacttg gtggagcacg   7680
acacgctagt ctactccaaa aatatcaaag atacagtctc agaagaccaa agggcaattg   7740 agactttttca acaaagggta atatccggaa acctcctcgg attccattgc ccagctatct   7800
gtcacttaat tgtgaagata gtggaaaagg aaggtggctc ctacaaatgc catcattgcg   7860
ataaaggaaa ggccatcgtt gaagatgcct ctgccgacag tggtcccaaa gatggacccc   7920
cacccacgag gagcatcgtg gtaaaagaag acgttccaac cacgtcttca aagcaagtgg   7980
attgatgtga tatctccact gacgtaaggg atgacgcaca atcccactat ccttcgcaag   8040
```

```
accccttcctc tatataagga agttcatttc atttggagag gataattatc caccatgtct   8100
ccggagagga gaccagttga gattaggcca gctacagcag ctgatatggc cgcggtttgt   8160
gatatcgtta accattacat tgagacgtct acagtgaact ttaggacaga gccacaaaca   8220
ccacaagagt ggattgatga tctagagagg ttgcaagata gatacccttg gttggttgct   8280
gaggttgagg gtgttgtggc tggtattgct tacgctgggc cctggaaggc taggaacgct   8340
tacgattgga cagttgagag tactgtttac gtgtcacata ggcatcaaag gttgggccta   8400
ggctccacat tgtacacaca tttgcttaag tctatggagg cgcaaggttt taagtcagtg   8460
gttgctgtta taggccttcc aaacgatcca tctgttaggt tgcatgaggc tctaggatac   8520
acagcgcggg gtacactgcg cgcagctgga tacaagcatg gtggatggca tgatgttggt   8580
ttttggcaaa gggattttga gttgccagct cctccaaggc cagtgaggcc agttacccag   8640
atctgactaa gatcgttcaa acatttggca ataaagtttc ttaagattga atcctgttgc   8700
cggtcttgcg atgattatca tataatttct gttgaattac gttaagcatg taataattaa   8760
catgtaatgc atgacgttat ttatgagatg ggttttatg attagagtcc cgcaattata    8820
catttaatac gcgatagaaa acaaaatata gcgcgcaaac taggataaat tatcgcgcgc   8880
ggtgtcatct atgttactag atcattagcc tgcaggcccg ggttagtcca tggctaatta   8940
gctaacggcc aggatcgccg cgtgagcctt tagcaactag ctagattaat taacgcaatc   9000
tgttattaag ttgtctaagc gtcaatttgt ttacaccaca atatatcctg ccaccagcca   9060
gccaacagct ccccgaccgg cagctcggca caaaatcacc actcgataca ggcagcccat   9120
cagaattaat tctcatgttt gacagcttat catcgactgc acggtgcacc aatgcttctg   9180
gcgtcaggca gccatcggaa gctgtggtat ggctgtgcag gtcgtaaatc actgcataat   9240
tcgtgtcgct caaggcgcac tcccgttctg gataatgttt tttgcgccga catcataacg   9300
gttctggcaa atattctgaa atgagctgtt gacaattaat catccggctc gtataatgtg   9360
tggaattgtg agcggataac aatttcacac aggaaacaga ccatgaggga agcgttgatc   9420
gccgaagtat cgactcaact atcagaggta gttggcgtca tcgagcgcca tctcgaaccg   9480
acgttgctgg ccgtacattt gtacggctcc gcagtggatg gcggcctgaa gccacacagt   9540
gatattgatt tgctggttac ggtgaccgta aggcttgatg aaacaacgcg gcgagctttg   9600
atcaacgacc ttttggaaac ttcggcttcc cctggagaga gcgagattct ccgcgctgta   9660
gaagtcacca ttgttgtgca cgacgacatc attccgtggc gttatccagc taagcgcgaa   9720
ctgcaatttg gagaatggca gcgcaatgac attcttgcag gtatcttcga gccagccacg   9780
atcgacattg atctggctat cttgctgaca aaagcaagag aacatagcgt tgccttggta   9840
ggtccagcgg cggaggaact ctttgatccg gttcctgaac aggatctatt tgaggcgcta   9900
aatgaaacct taacgctatg gaactcgccg cccgactggg ctggcgatga gcgaaatgta   9960
gtgcttacgt tgtcccgcat ttggtacagc gcagtaaccg gcaaaatcgc gccgaaggat  10020
gtcgctgccg actgggcaat ggagcgcctg ccggcccagt atcagcccgt catacttgaa  10080
gctaggcagg cttatcttgg acaagaagat cgcttggcct cgcgcgcaga tcagttggaa  10140
gaatttgttc actacgtgaa aggcgagatc accaaagtag tcggcaaata aagctctagt  10200
ggatctccgt acccagggat ctggctcgcg gcggacgcac gacgccgggg cgagaccata  10260
ggcgatctcc taaatcaata gtagctgtaa cctcgaagcg tttcacttgt aacaacgatt  10320
gagaattttt gtcataaaat tgaaatactt ggttcgcatt tttgtcatcc gcggtcagcc  10380
gcaattctga cgaactgccc atttagctgg agatgattgt acatccttca cgtgaaaatt  10440
```

```
tctcaagcgc tgtgaacaag ggttcagatt ttagattgaa aggtgagccg ttgaaacacg   10500
ttcttcttgt cgatgacgac gtcgctatgc ggcatcttat tattgaatac cttacgatcc   10560
acgccttcaa agtgaccgcg gtagccgaca gcacccagtt cacaagagta ctctcttccg   10620
cgacggtcga tgtcgtggtt gttgatctag atttaggtcg tgaagatggg ctcgagatcc   10680
ttcgtaatct ggcggcaaag tctgatattc caatcataat tatcagtggc gaccgccttg   10740
aggagacgga taaagttgtt gcactcgagc taggagcaag tgattttatc gctaagccgt   10800
tcagtatcag agagtttcta gcacgcattc gggttgcctt gcgcgtgcgc cccaacgttg   10860
tccgctccaa agaccgacgg tcttttttgtt ttactgactg gacacttaat ctcaggcaac   10920
gtcgcttgat gtccgaagct ggcggtgagg tgaaacttac ggcaggtgag ttcaatcttc   10980
tcctcgcgtt tttagagaaa ccccgcgacg ttctatcgcg cgagcaactt ctcattgcca   11040
gtcgagtacg cgacgaggag gtttatgaca ggagtataga tgttctcatt ttgaggctgc   11100
gccgcaaact tgaggcagat ccgtcaagcc ctcaactgat aaaaacagca agaggtgccg   11160
gttatttctt tgacgcggac gtgcaggttt cgcacggggg gacgatggca gcctgagcca   11220
attcccagat ccccgaggaa tcggcgtgag cggtcgcaaa ccatccggcc cggtacaaat   11280
cggcgcggcg ctgggtgatg acctggtgga gaagttgaag gccgcgcagg ccgcccagcg   11340
gcaacgcatc gaggcagaag cacgccccgg tgaatcgtgg caagcggccg ctgatcgaat   11400
ccgcaaagaa tcccggcaac cgccggcagc cggtgcgccg tcgattagga agccgcccaa   11460
gggcgacgag caaccagatt ttttcgttcc gatgctctat gacgtgggca cccgcgatag   11520
tcgcagcatc atggacgtgg ccgttttccg tctgtcgaag cgtgaccgac gagctggcga   11580
ggtgatccgc tacgagcttc cagacgggca cgtagaggtt tccgcagggc cggccggcat   11640
ggccagtgtg tgggattacg acctggtact gatggcggtt tcccatctaa ccgaatccat   11700
gaaccgatac cggaagggga agggagacaa gcccggccgc gtgttccgtc cacacgttgc   11760
ggacgtactc aagttctgcc ggcgagccga tggcggaaag cagaaagacg acctggtaga   11820
aacctgcatt cggttaaaca ccacgcacgt tgccatgcag cgtacgaaga aggccaagaa   11880
cggccgcctg gtgacggtat ccgagggtga agccttgatt agccgctaca agatcgtaaa   11940
gagcgaaacc gggcggccgg agtacatcga gatcgagctg gctgattgga tgtaccgcga   12000
gatcacagaa ggcaagaacc cggacgtgct gacggttcac cccgattact ttttgatcga   12060
tcccggcatc ggccgttttc tctaccgcct ggcacgccgc gccgcaggca aggcagaagc   12120
cagatggttg ttcaagacga tctacgaacg cagtggcagc gccggagagt tcaagaagtt   12180
ctgtttcacc gtgcgcaagc tgatcgggtc aaatgacctg ccggagtacg atttgaagga   12240
ggaggcgggg caggctggcc cgatcctagt catgcgctac cgcaacctga tcgagggcga   12300
agcatccgcc ggttcctaat gtacggagca gatgctaggg caaattgccc tagcagggga   12360
aaaaggtcga aaaggtctct ttcctgtgga tagcacgtac attgggaacc caaagccgta   12420
cattgggaac cggaacccgt acattgggaa cccaaagccg tacattggga accggtcaca   12480
catgtaagtg actgatataa aagagaaaaa aggcgatttt tccgcctaaa actctttaaa   12540
acttattaaa actcttaaaa cccgcctggc ctgtgcataa ctgtctgacc agcgcacagc   12600
cgaagagctg caaaaagcgc ctacccttcg gtcgctgcgc tccctacgcc ccgccgcttc   12660
gcgtcggcct atcgcggccg ctggccgctc aaaaatggct ggcctacggc caggcaatct   12720
accagggcgc ggacaagccg cgccgtcgcc actcgaccgc cggcgctgag gtctgcctcg   12780
```

```
tgaagaaggt gttgctgact cataccaggc ctgaatcgcc ccatcatcca gccagaaagt    12840
gagggagcca cggttgatga gagctttgtt gtaggtggac cagttggtga ttttgaactt    12900
ttgctttgcc acggaacggt ctgcgttgtc gggaagatgc gtgatctgat ccttcaactc    12960
agcaaaagtt cgatttattc aacaaagccg ccgtcccgtc aagtcagcgt aatgctctgc    13020
cagtgttaca accaattaac caattctgat tagaaaaact catcgagcat caaatgaaac    13080
tgcaatttat tcatatcagg attatcaata ccatattttt gaaaaagccg tttctgtaat    13140
gaaggagaaa actcaccgag gcagttccat aggatggcaa gatcctggta tcggtctgcg    13200
attccgactc gtccaacatc aatacaacct attaatttcc cctcgtcaaa ataaggtta     13260 tcaagtgaga aatcaccatg agtgacgact gaatccggtg agaatggcaa aagctctgca    13320
ttaatgaatc ggccaacgcg cggggagagg cggtttgcgt attgggcgct cttccgcttc    13380
ctcgctcact gactcgctgc gctcggtcgt tcggctgcgg cgagcggtat cagctcactc    13440
aaaggcggta atacggttat ccacagaatc aggggataac gcaggaaaga acatgtgagc    13500
aaaaggccag caaaaggcca ggaaccgtaa aaaggccgcg ttgctggcgt ttttccatag    13560
gctccgcccc cctgacgagc atcacaaaaa tcgacgctca agtcagaggt ggcgaaaccc    13620
gacaggacta taaagatacc aggcgtttcc ccctggaagc tccctcgtgc gctctcctgt    13680
tccgaccctg ccgcttaccg gatacctgtc cgcctttctc ccttcgggaa gcgtggcgct    13740
ttctcatagc tcacgctgta ggtatctcag ttcggtgtag tcgttcgct ccaagctggg     13800 ctgtgtgcac gaaccccccg ttcagcccga ccgctgcgcc ttatccggta actatcgtct    13860
tgagtccaac ccggtaagac acgacttatc gccactggca gcagccactg gtaacaggat    13920
tagcagagcg aggtatgtag gcggtgctac agagttcttg aagtggtggc ctaactacgg    13980
ctacactaga agaacagtat ttggtatctg cgctctgctg aagccagtta ccttcggaaa    14040
aagagttggt agctcttgat ccggcaaaca aaccaccgct ggtagcggtg ttttttttgt    14100
ttgcaagcag cagattacgc gcagaaaaaa aggatctcaa gaagatcctt tgatcttttc    14160
tacggggtct gacgctcagt ggaacgaaaa ctcacgttaa gggattttgg tcatgagatt    14220
atcaaaaagg atcttcacct agatcctttt gatccggaat ta                      14262
```

US 10,844,396 B2

NUCLEIC ACID CONSTRUCT FOR CONFERRING HERBICIDE TOLERANCE IN PLANTS

STATEMENT REGARDING ELECTRONIC SUBMISSION OF A SEQUENCE LISTING

A sequence listing in ASCII text format, submitted under 37 C.F.R. § 1.821, entitled "80561 ST25.txt", 31 kilobytes in size, generated on Jan. 29, 2016 and filed via EFS-Web is provided in lieu of a paper copy. This sequence listing is hereby incorporated by reference into the specification for its disclosures.

FIELD OF THE INVENTION

The present invention generally relates to transgenic plants with herbicide tolerance. In particular, the present invention provides a construct which confers resistance to the herbicides glyphosate and glufosinate when introduced into a plant by transformation.

BACKGROUND OF THE INVENTION

Herbicide tolerant transgenic plants are widely commercially available. Over 90% of commercially grown maize and soybean in the United States are herbicide tolerant transgenic plants. Widespread usage of a single herbicide tolerant trait can result in breakdown of the effectiveness of the herbicide. To address this, transgenic plants can be created which carry herbicide tolerance against multiple classes of herbicide.

One major herbicide tolerance trait is conferred by transgenic expression of glutamine synthetase. Glutamine synthetase (GS) constitutes in most plants one of the essential enzymes for the development and life of plant cells. It is known that GS converts glutamate into glutamine. GS is involved in an efficient pathway in most plants for the detoxification of ammonia released by nitrate reduction, amino acid degradation or photorespiration. Therefore potent inhibitors of GS are very toxic to plant cells and can be used as broad-spectrum herbicides. A class of herbicides, which include phosphinothricin and glufosinate, comprise a GS inhibitor as an active ingredient. Transgenic plants have been made tolerant to this class of herbicides through the introduction of a gene encoding a phosphinothricin acetyltransferase (PAT). The gene PAT is derived from *Streptomyces viridochromogenes* and confers tolerance to glufosinate. (U.S. Pat. Nos. 5,531,236, 5,646,024, 5,648,477, and 5,276,268)

A second broad-spectrum herbicide is N-phosphonomethyl-glycine, commonly referred to as glyphosate. Glyphosate inhibits the shikimic acid pathway which leads to the biosynthesis of aromatic compounds including amino acids and vitamins. Specifically, glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS). Glyphosate tolerant plants can be produced by introducing an EPSPS which is tolerant to glyphosate. One example of this is the maize event GA21 (U.S. Pat. No. 6,040,497), which transgenically expresses a modified maize EPSPS gene (here referred to as ZmEPSPS; U.S. Pat. No. 6,566,587).

Glyphosate is a foliar applied, post-emergence herbicide. It is phloem-mobile, and is known to localize in the meristems and young, actively growing tissues, including roots, leaves, and male reproductive tissues (Hetherington et al., 1999, J of Experimental Botany, 50: 1567-1576). In transgenic plants expressing an EPSPS gene to confer glyphosate tolerance, there can be issues in recovering fully male-fertile transgenic events at commercial rates of glyphosate application (Heck et al., 2005, Crop Science, 44: 329-339; Green, 2009, Weed Science, 57: 108-117). The creation of a commercial construct comprising a gene which confers tolerance to glyphosate without compromising male fertility is unpredictable and requires substantial testing and experimentation.

Transgenic plants which carry multiple herbicide tolerance traits would provide the grower with more options to manage weeds and crop cycles. A strategy to provide growers with such plants is to "stack" herbicide tolerance traits. Currently, transgenic traits are frequently stacked through breeding and subsequent screening to get multiple transgenic traits into a single commercial germplasm. These breeding and screening steps are required for every variety of germplasm into which introduction of these two traits is desirable. Additionally, for many agronomically important crops, these two traits need to be maintained as hybrids for dozens of germplasm varieties. Finally, factors such as the genetic linkage of undesirable traits or genetic recombination may complicate the introduction of two traits from two distinct loci into a single germplasm variety. Therefore, it would be advantageous to create a nucleic acid molecule which carries multiple herbicide tolerance traits and can be introduced at a single locus in the genome of the transgenic plant.

SUMMARY OF THE INVENTION

The present invention provides an optionally isolated nucleic acid molecule that is at least 90% identical to SEQ ID NO: 1. The present invention also provides for a nucleic acid molecule, a chimeric nucleic acid molecule, and/or a recombinant nucleic acid construct or vector which comprise, consist, or consist essentially of SEQ ID NO: 1. The present invention also provides for a nucleic acid molecule, a chimeric nucleic acid molecule, and/or a recombinant nucleic acid construct or vector which comprise, consist, or consist essentially of a nucleic acid sequence that is at least 90% identical to SEQ ID NO: 1.

The present invention also provides for use of a nucleic acid molecule of the invention as described herein, wherein expression of said nucleic acid molecule in a cell confers herbicide tolerance.

The present invention also provides for a transgenic host cell comprising a nucleic acid molecule of the invention as described herein. The transgenic host cell described above may be a bacterial cell or a plant cell. The transgenic bacterial cell may be an *Escherichia coli, Bacillus thuringiensis, Bacillus subtilis, Bacillus megaterium; Bacillus cereus, Agrobacterium* ssp. or a *Pseudomonas* ssp. cell. The transgenic plant cell may be found within a transgenic plant, plant part, plant tissue, or plant cell culture. The transgenic plant may be a monocotyledonous or dicotyledonous plant. The transgenic plant may be selected from the group comprising maize, sorghum, wheat, sunflower, tomato, crucifers, oat, turf grass, pasture grass, peppers, potato, cotton, rice, soybean, sugarcane, sugar beet, tobacco, barley, and oilseed rape.

The present invention also provides for a progeny of any generation of a transgenic plant, wherein said transgenic plant comprises a nucleic acid molecule of the invention as described herein. The present invention also provides for a transgenic seed and for a transgenic propagule from said transgenic plant.

The present invention also provides for a method of producing an herbicide tolerant transgenic plant, comprising introducing a nucleic acid molecule of the invention as described herein into a plant thereby producing a transgenic plant, wherein the nucleic acid molecule is capable of expressing herbicide tolerance genes in an amount that controls weeds.

The present invention also provides for a method of producing an herbicide tolerant plant, comprising the steps of (a) providing a nucleic acid molecule of the invention as described herein; (b) introducing into a plant, tissue culture, or a plant cell the nucleic acid molecule of step (a) to obtain a transformed plant, transformed tissue culture, or a transformed cell having herbicide tolerance; and (c) growing said transformed plant or regenerating a transformed plant from the transformed tissue culture or transformed plant cell, so a herbicide tolerant plant is produced. The present invention also provides for a method of producing transgenic seed from the transgenic plant described above, where the plant is cultured or grown under appropriate conditions to produce progeny seed which is transgenic.

The present invention also provides for a method of producing progeny of any generation of an herbicide tolerant fertile transgenic plant, comprising the steps of: (a) obtaining a herbicide tolerant fertile transgenic plant comprising a nucleic acid molecule of the invention as described herein; (b) collecting transgenic seed from said transgenic plant; (c) planting the collected transgenic seed; and (d) growing the progeny transgenic plants from said seed, wherein said progeny has enhanced herbicide tolerance relative to a non-transformed plant.

The present invention also provides for a method for producing a plant with herbicide tolerance, comprising the steps of: (a) sexually crossing a first parent plant with a second parent plant, wherein said first or second parent plant is a transgenic plant comprising a nucleic acid molecule of the invention as described herein; (b) selecting a first generation progeny plant with herbicide tolerance; (c) selfing the first generation progeny plant, thereby producing a plurality of second generation progeny plants; and (d) selecting from the second generation progeny plants a plant with herbicide tolerance, wherein the second generation progeny plants comprise a nucleic acid molecule of the invention as described herein.

BRIEF DESCRIPTION OF THE DRAWINGS

FIG. 1 is a representation of binary vector 18857, whose nucleic acid sequence is SEQ ID NO: 2.

BRIEF DESCRIPTION OF SEQUENCES IN THE SEQUENCE LISTING

SEQ ID NO: 1 is the nucleic acid sequence of the transgene and comprises expression cassettes comprising ZmEPSPS and PAT coding sequences.

SEQ ID NO: 2 is the nucleic acid sequence of the binary vector 18857.

DETAILED DESCRIPTION OF THE INVENTION

It is to be understood that this invention is not limited to the particular methodology, protocols, cell lines, plant species or genera, constructs, and reagents described herein as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means ±1° C., preferably ±0.5° C. Where the term "about" is used in the context of this invention (e.g., in combinations with temperature or molecular weight values) the exact value (i.e., without "about") is preferred.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

"cDNA" refers to a single-stranded or a double-stranded DNA that is complementary to and derived from mRNA. The terms "messenger RNA" or "mRNA" refer to RNA that does not comprise introns and that can be translated into a protein by the cell. The terms "protein," "peptide" and "polypeptide" are used interchangeably herein.

A "control plant" or "control" as used herein may be a non-transgenic plant of the parental line used to generate a transgenic plant herein. A control plant may in some cases be a transgenic plant line that includes an empty vector or marker gene, but does not contain the recombinant polynucleotide of the present invention that is expressed in the transgenic plant being evaluated. A control plant in other cases is a transgenic plant expressing the gene with a constitutive promoter. In general, a control plant is a plant of the same line or variety as the transgenic plant being tested, lacking the specific trait-conferring, recombinant DNA that characterizes the transgenic plant. Such a progenitor plant that lacks that specific trait-conferring recombinant DNA can be a natural, wild-type plant, an elite, non-transgenic plant, or a transgenic plant without the specific trait-conferring, recombinant DNA that characterizes the transgenic plant. The progenitor plant lacking the specific, trait-conferring recombinant DNA can be a sibling of a transgenic plant having the specific, trait-conferring recombinant DNA. Such a progenitor sibling plant may include other recombinant DNA.

As used herein, the term "corn" means Zea mays or maize and includes all plant varieties that can be bred with corn, including wild maize species.

The term "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The term "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

The term "chimeric construct", "chimeric gene", "chimeric polynucleotide" or chimeric nucleic acid" (and similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains (1) polynucleotides (e.g., DNA), including regulatory and coding polynucleotides that are not found together in nature (i.e., at least one of polynucleotides is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In a preferred aspect of the present invention the chimeric construct, chimeric gene, chimeric polynucleotide or chimeric nucleic acid comprises an expression cassette comprising a polynucleotides of the present invention under the control of regulatory polynucleotides, particularly under the control of regulatory polynucleotides functional in plants.

The term "chromosome" is used herein as recognized in the art as meaning the self-replicating genetic structure in the cellular nucleus containing the cellular DNA and bearing the linear array of genes.

A "coding polynucleotide" is a polynucleotide that is transcribed into RNA, such as mRNA, rRNA, tRNA, snRNA, sense RNA or antisense RNA. Preferably the RNA is then translated in an organism to produce a protein. It may constitute an "uninterrupted coding polynucleotide", i.e., lacking an intron, such as in a cDNA, or it may include one or more introns bounded by appropriate splice junctions. An "intron" is a poly(ribo)nucleotide which is contained in the primary transcript but which is removed through cleavage and religation of the RNA within the cell to create the mature mRNA that can be translated into a protein.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

"Expression cassette" as used herein means a nucleic acid molecule capable of directing expression of a particular polynucleotide or polynucleotides in an appropriate host cell, comprising a promoter operably linked to the polynucleotide or polynucleotides of interest which is/are operably linked to termination signals. It also typically comprises polynucleotides required for proper translation of the polynucleotide or polynucleotides of interest. The expression cassette may also comprise polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the particular polynucleotide of the expression cassette does not occur naturally in the host cell and must have been introduced into the host cell or an ancestor of the host cell by a transformation process known in the art. The expression of the polynucleotide(s) in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is defined herein as a hereditary unit consisting of a polynucleotide that occupies a specific location on a chromosome and that contains the genetic instruction for a particular characteristic or trait in an organism[, or such hereditary unit from a group of heterologous organisms depending on context.]

"Genetic engineering", "transformation" and "genetic modification" are all used herein as synonyms for the transfer of isolated and cloned genes into the DNA, usually the chromosomal DNA or genome, of another organism.

A "transgene" refers to a gene, polynucleotide or nucleic acid introduced into the genome of an organism by genetic manipulation in order to alter its genotype. Transgenes may include, for example, genes, polynucleotides or nucleic acids that are either heterologous or homologous to the particular plant to be transformed. Additionally, transgenes may comprise native genes inserted into a non-native organism, or chimeric genes, polynucleotides or nucleic acids.

The term "genotype" refers to the genetic constitution of a cell or organism. An individual's "genotype for a set of genetic markers" includes the specific alleles, for one or more genetic marker loci, present in the individual. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative trait as defined herein). Thus, in some embodiments a genotype comprises a sum of one or more alleles present within an individual at one or more genetic loci of a quantitative trait. In some embodiments, a genotype is expressed in terms of a haplotype (defined herein below).

"Transformed," "transgenic," and "recombinant" are used interchangeably and each refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

"Wild-type" refers to the normal gene, virus, or organism found in nature without any mutation or modification.

The term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

As used herein, "propagule" refers to any material that is used for propagating a plant, preferably a transgenic plant, more preferably a transgenic plant comprising SEQ ID NO: 1. A propagule may be a seed, cutting, or plurality of cells from a transgenic plant, which can be used to produce a crop of transgenic plants.

As used herein "plant sample" or "biological sample" refers to either intact or non-intact (e.g. milled seed or plant tissue, chopped plant tissue, lyophilized tissue) plant tissue. It may also be an extract comprising intact or non-intact seed or plant tissue. The biological sample or extract may be selected from the group consisting of corn flour, corn meal, corn syrup, corn oil, corn starch, and cereals manufactured in whole or in part to contain corn by-products.

The term "heterologous" when used in reference to a gene or nucleic acid refers to a gene encoding a factor that is not in its natural environment (i.e., has been altered by the hand of man). For example, a heterologous gene may include a gene from one species introduced into another species. A heterologous gene may also include a gene native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, in embodiments, a "heterologous" polynucleotide is a polynucleotide not naturally associated with a host cell into which it is introduced, including non-naturally occurring multiple copies of a naturally occurring polynucleotide.

"Identity" or "percent identity" refers to the degree of similarity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

The term "homology" in the context of the invention refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For an amino acid sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, or at least 30% identical, or at least 40% identical, or at least 50% identical, or at least 60% identical, or at least 70% identical, or at least 80% identical, or at least 88% identical, or at least 90% identical, or at least 92% identical, or at least 95% identical, across any substantial region of the molecule (DNA, RNA, or protein molecule).

One example of an algorithm that is suitable for determining percent sequence identity and sequence similarity is the BLAST algorithm, which is described in Altschul et al., J. Mol. Biol. 215: 403 410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873 5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

For DNA-DNA hybrids, the Tm can be approximated from the equation of Meinkoth and Wahl, Anal. Biochem., 138:267-84 (1984): Tm=81.5° C.+16.6 (log M)+0.41 (% GC)−0.61 (% formamide)−500/L; where M is the molarity of monovalent cations, % GC is the percentage of guanosine and cytosine nucleotides in the DNA, % formamide is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired degree of identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, highly stringent conditions can utilize a hybridization and/or wash at the thermal melting point (Tm) or 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). If the desired degree of mismatching results in a Tm of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M NaPO4, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code). A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

The terms "complementary" or "complementarity" (and similar terms), as used herein, refer to the natural binding of polynucleotides under permissive salt and temperature conditions by base-pairing. For example, the sequence "A-G-T" binds to the complementary sequence "T-C-A." Complementarity between two single-stranded molecules may be partial, in which only some of the nucleotides bind, or it may be complete when total complementarity exists between the single stranded molecules. The degree of complementarity between nucleic acid strands has significant effects on the efficiency and strength of hybridization between the molecules.

As used herein, the term "substantially complementary" (and similar terms) means that two nucleic acid sequences are at least about 50%, 60%, 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein).

The term "isolated", when used in the context of the nucleic acid molecules or polynucleotides of the present invention, refers to a polynucleotide that is identified within and isolated/separated from its chromosomal polynucleotide context within the respective source organism. An isolated nucleic acid or polynucleotide is not a nucleic acid as it occurs in its natural context, if it indeed has a naturally occurring counterpart. In contrast, non-isolated nucleic acids are nucleic acids such as DNA and RNA, which are found in the state they exist in nature. For example, a given polynucleotide (e.g., a gene) is found on the host cell chromosome in proximity to neighboring genes. The isolated nucleic acid molecule may be present in single-stranded or double-stranded form. Alternatively, it may contain both the sense and antisense strands (i.e., the nucleic acid molecule may be double-stranded). In a preferred embodiment, the nucleic acid molecules of the present invention are understood to be isolated.

The term "locus" refers to a position (e.g., of a gene, a genetic marker, or the like) on a chromosome of a given species.

The term "linkage", and grammatical variants thereof, refers to the tendency of alleles at different loci on the same chromosome to segregate together more often than would be expected by chance if their transmission were independent, in some embodiments as a consequence of their physical proximity. The phrase "linkage disequilibrium" (also called "allelic association") refers to a phenomenon wherein particular alleles at two or more loci tend to remain together in linkage groups when segregating from parents to offspring with a greater frequency than expected from their individual frequencies in a given population. For example, a genetic marker allele and a QTL allele can show linkage disequilibrium when they occur together with frequencies greater than those predicted from the individual allele frequencies. Linkage disequilibrium can occur for several reasons including, but not limited to the alleles being in close proximity on a chromosome. The term "linkage group" refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous to (the physical entity of) chromosome.

The phrase "nucleic acid" or "polynucleotide" refers to any physical string of monomer units that can be corresponded to a string of nucleotides, including a polymer of nucleotides (e.g., a typical DNA polymer or polydeoxyribonucleotide or RNA polymer or polyribonucleotide), modified oligonucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated.

"PCR (polymerase chain reaction)" is understood within the scope of the invention to refer to a method of producing relatively large amounts of specific regions of DNA, thereby making possible various analyses that are based on those regions.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

The term "promoter" refers to a polynucleotide, usually upstream (5') of its coding polynucleotide, which controls the expression of the coding polynucleotide by providing the recognition for RNA polymerase and other factors required for proper transcription. "Constitutive promoter" refers to a promoter that is able to express the open reading frame (ORF) that it controls in all or nearly all of the plant tissues during all or nearly all developmental stages of the plant (referred to as "constitutive expression"). "Regulated promoter" refers to promoters that direct gene expression not constitutively, but in a temporally- and/or spatially-regulated manner, and includes tissue-specific, tissue-preferred and inducible promoters. It includes natural and synthetic polynucleotides as well as polynucleotides which may be a combination of synthetic and natural polynucleotides. Different promoters may direct the expression of a gene in different tissues or cell types, or at different stages of development, or in response to different environmental conditions.

"Tissue-specific promoter" or "tissue-preferred promoter" refers to regulated promoters that are not expressed in all plant cells but only or preferentially in one or more cell types in specific organs (such as leaves or seeds), specific tissues (such as embryo or cotyledon), or specific cell types (such as leaf parenchyma or seed storage cells). These terms also include promoters that are temporally regulated, such as in early or late embryogenesis, during fruit ripening in developing seeds or fruit, in fully differentiated leaf, or at the onset of senescence. Those skilled in the art will understand that tissue-specific promoters need not exhibit an absolute tissue-specificity, but mediate transcriptional activation in most plant parts at a level of about 1% or less of the level reached in the part of the plant in which transcription is most active.

An "enhancer" or "transcriptional enhancer" is a nucleotide sequence that can stimulate promoter activity and can be an innate element of the promoter or a heterologous element inserted to enhance the level or tissue specificity of a promoter. The primary sequence can be present on either strand of a double-stranded DNA molecule, and is capable of functioning even when placed either upstream or downstream from the promoter.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translational enhancer sequences, introns, and polyadenylation signal sequences. They include natural and synthetic sequences as well as sequences which may be a combination of synthetic and natural sequences. Regulatory sequences may determine expression level, the spatial and temporal pattern of expression and, for a subset of promoters, expression under inductive conditions (regulation by external factors such as light, temperature, chemicals and hormones). Regulatory sequences may be short regions of DNA sequence 6-100 base pairs that define the binding sites for trans-acting factors, such as transcription factors. Regulatory sequences may also be enhancers, longer regions of DNA sequence that can act from a distance from the core promoter region, sometimes over several kilobases from the core region. Regulatory sequence activity may be influenced by trans-acting factors including general transcription machinery, transcription factors and chromatin assembly factors.

"Cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

A "transcriptional terminator" is responsible for the termination of transcription beyond the coding region and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

The term "translational enhancer sequence" refers to that DNA sequence portion of a gene between the promoter and coding sequence that is transcribed into RNA and is present in the fully processed mRNA upstream (5') of the translation start codon. The translational enhancer sequence may affect processing of the primary transcript to mRNA, mRNA stability or translation efficiency.

As used herein, gene or trait "stacking" is combining desired genes or traits into one transgenic plant line. As one approach, plant breeders stack transgenic traits by making crosses between parents that each have a desired trait and then identifying offspring that have both of these desired traits (so-called "breeding stacks"). Another way to stack genes is by transferring two or more genes into the cell nucleus of a plant at the same time during transformation. Another way to stack genes is by re-transforming a transgenic plant with another gene of interest. For example, gene stacking can be used to combine two different insect resistance traits, an insect resistance trait and a disease resistance trait, or a herbicide resistance trait (such as, for example, BO 1). The use of a selectable marker in addition to a gene of interest would also be considered gene stacking.

The term "plant" includes reference to whole plants, plant organs, tissues (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans,* Fragaria, Lotus, *Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

The term "transgenic plant" includes reference to a plant, which comprises within its genome a heterologous nucleic acid sequence. Generally, the heterologous nucleic acid sequence is stably integrated within the genome such that the nucleic acid sequence is passed on to successive generations. The heterologous nucleic acid sequence may be integrated into the genome alone or as part of a recombinant expression cassette. "Transgenic" is used herein to include any cell, cell line, callus, tissue, plant part or plant, the genotype of which has been altered by the presence of a heterologous nucleic acid sequence, including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

The term "yield" may include reference to bushels per acre of a grain crop at harvest, as adjusted for grain moisture (15% typically for maize, for example), and the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated. Yield can be affected by many properties including without limitation, plant height, pod number, pod position on the plant, number of internodes, incidence of pod shatter, grain size, efficiency of nodulation and nitrogen fixation, efficiency of nutrient assimilation, carbon assimilation, plant architecture, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Yield of a plant of the can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are common practice in the art In certain embodiments of the invention yield may be increased in stressed and/or non-stressed conditions.

The term "vector" or "construct" includes reference to a nucleic acid used in transfection of a host cell and into which can be inserted a polynucleotide. Vectors are often replicons. Expression vectors permit transcription of a nucleic acid inserted therein. "Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

The term "transformation" as used herein refers to the transfer of a nucleic acid fragment into the genome of a host cell, resulting in genetically stable inheritance. In some particular embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or a combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al 1993, Plant Cell 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen and Willmitzer 1988, Nucleic Acids Res 16: 9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of nontransformed tissue. Positive selection can be of many types from inactive forms of plant growth regulators that are then converted to active forms by the transferred enzyme to alternative carbohydrate sources that are not utilized efficiently by the nontransformed cells, for example mannose, which then become available upon transformation with an enzyme, for example phosphomannose isomerase, that allows them to be metabolized. Nontransformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90: 217-23), spectinomycin (Svab and Maliga 1993, Plant Mol Biol 14: 197-205), streptomycin (Maliga et al. 1988, Mol Gen Genet 214: 456-459), hygromycin B (Waldron et al. 1985, Plant Mol Biol 5: 103-108), bleomycin (Hille et al. 1986, Plant Mol Biol 7: 171-176), sulphonamides (Guerineau et al. 1990, Plant Mol Biol 15: 127-136), streptothricin (Jelenska et al. 2000, Plant Cell Rep 19: 298-303), or chloramphenicol (De Block et al. 1984, EMBO J 3: 1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. No. 5,561,236); aryloxy alkanoate dioxygenase or AAD-1, AAD-12, or AAD-13 which confer resistance to 2,4-D; genes such as *Pseudomonas* HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone); and genes conferring resistance to dicamba, such as dicamba monoxygenase (Herman et al. 2005, J Biol Chem 280: 24759-24767 and U.S. Pat. No. 7,812,224 and related applications and patents). Other examples of selectable markers can be found in Sundar and Sakthivel (2008, J Plant Physiology 165: 1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37: 287-96). Finally, other selection systems may use hormone-free medium as the selection agent. One non-limiting example the maize homeobox gene knl, whose ectopic expression results in a 3-fold increase in transformation efficiency (Luo et al. 2006, Plant Cell Rep 25: 403-409). Examples of various selectable markers and genes encoding them are disclosed in Miki and McHugh (J Biotechnol, 2004, 107: 193-232; incorporated by reference).

In some embodiments of the invention, the selectable marker may be plant derived. An example of a selectable marker which can be plant derived includes, but is not limited to, 5-enolpyruvylshikimate-3-phosphate synthase (EPSPS). The enzyme 5-enolpyruvylshikimate-3-phosphate synthase (EPSPS) catalyzes an essential step in the shikimate pathway common to aromatic amino acid biosynthesis in plants. The herbicide glyphosate inhibits EPSPS, thereby killing the plant. Transgenic glyphosate-tolerant plants can be created by the introduction of a modified EPSPS transgene which is not affected by glyphosate (for example, U.S. Pat. No. 6,040,497; incorporated by reference). Other examples of a modified plant EPSPS which can be used as a selectable marker in the presence of glyphosate includes a P106L mutant of rice EPSPS (Zhou et al 2006, Plant Physiol 140: 184-195) and a P106S mutation in goosegrass EPSPS (Baerson et al 2002, Plant Physiol 129: 1265-1275). Other sources of EPSPS which are not plant derived and can be used to confer glyphosate tolerance include but are not limited to an EPSPS P101S mutant from *Salmonella typhimurium* (Comai et al 1985, Nature 317: 741-744) and a mutated version of CP4 EPSPS from *Agrobacterium* sp. Strain CP4 (Funke et al 2006, PNAS 103: 13010-13015). Although the plant EPSPS gene is nuclear, the mature enzyme is localized in the chloroplast (Mousdale and Coggins 1985, Planta 163:241-249). EPSPS is synthesized as a preprotein containing a transit peptide, and the precursor is then transported into the chloroplast stroma and proteolytically processed to yield the mature enzyme (della-Cioppa et al. 1986, PNAS 83: 6873-6877). Therefore, to create a transgenic plant which has tolerance to glyphosate, a suitably mutated version of EPSPS which correctly translocates to the chloroplast could be introduced. Such a transgenic plant then has a native, genomic EPSPS gene as well as the mutated EPSPS transgene. Glyphosate could then be used as a selection agent during the transformation and regeneration process, whereby only those plants or plant tissue that are successfully transformed with the mutated EPSPS transgene survive.

As used herein, the term transgenic "event" refers to a recombinant plant produced by transformation and regeneration of a plant cell or tissue with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. Normally, transformation of plant tissue produces multiple events, each of which represent insertion of a DNA construct into a different location in the genome of a plant cell. Based on the expression of the transgene or other desirable characteristics, a particular event is selected.

One skilled in the art will recognize that the transgenic genotype of the invention can be introgressed by breeding into other plant lines comprising different transgenic or non-transgenic genotypes. For example, a corn inbred comprising the transgenic genotype of the invention can be crossed with a corn inbred comprising the transgenic genotype of the lepidopteran resistant MIR162 event, which is known in the art, thus producing corn seed that comprises both the transgenic genotype of the invention and the MIR162 transgenic genotype. It will be further recognized that other combinations can be made with the transgenic genotype of the invention and thus this example should not be viewed as limiting.

The transgenic genotype of the invention can be introgressed from the initially transformed plant, such as a corn plant, into an inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Although commercial events exist which carry either the PAT gene (such as Bt11, U.S. Pat. Nos. 6,114,608 and 6,403,865) or the ZmEPSPS gene (such as GA21, U.S. Pat. No. 6,040,497), the ability to introduce both genes at a single locus in a plant genome would provide significant advantages. Currently, the creation of a commercially useful transgenic plant that comprises both PAT and ZmEPSPS transgenes requires multiple breeding steps and a significant amount of screening to identify the correct genotype in the correct germplasm. These breeding and screening steps are required for every variety of germplasm into which introduction of these two traits is desirable. Additionally, for many agronomically important crops, these two traits need to be maintained as hybrids for dozens of germplasm varieties. Finally, factors such as the genetic linkage of undesirable traits or genetic recombination may complicate the introduction of two traits from two distinct loci into a single germplasm variety. Therefore, it would be advantageous to create a nucleic acid molecule which carries multiple herbicide tolerance traits and can be introduced at a single locus in the genome of the transgenic plant.

Different constructs were produced to determine the efficacy of the PAT and ZmEPSPS genes in the context of different expression cassettes. Surprisingly, one vector, 18857, conferred excellent herbicide tolerance without any negative effects on the vegetative development or the fertility of the transgenic plant. The transgene from vector 18857 is SEQ ID NO: 1. This transgene comprises two expression cassettes.

A skilled person would recognize that during the insertion of a nucleic acid molecule, such as SEQ ID NO: 1, into a cell, the 5' and/or 3' ends of the inserted molecule may be deleted or rearranged. Such deletions or rearrangements may not affect the function of the inserted molecule, and these relatively small changes result in an inserted molecule that may be considered to be essentially the same as the starting molecule. A skilled person would also recognize that the nucleic acid molecule, such as one comprising SEQ ID NO: 1, may undergo full or partial rearrangement or duplication during the insertion event, such that the inserted molecule is a full or partial rearrangement or duplication of the starting nucleic acid molecule. A skilled person would recognize that this inserted molecule may still have the same characteristics and/or traits as the starting molecule, such that the transformed cell or resulting transformed plant may still be desirable.

A skilled person would recognize that a transgene for commercial use, such as a nucleic acid molecule that comprises SEQ ID NO: 1, may need relatively minor modifications to the nucleic acid sequence to comply with governmental regulatory standards. Such modifications would not affect the function of the molecule. A skilled person would recognize that the modified nucleic acid molecule would be essentially the same as the starting molecule.

Therefore, the invention encompasses a nucleic acid molecule substantially identical to SEQ ID NO: 1, wherein certain nucleotides of SEQ ID NO: 1 are deleted, substituted or rearranged, resulting in a mutated SEQ ID NO:1 and wherein the functionality of the mutated SEQ ID NO:1 is the same as the starting molecule. The present invention also provides for a nucleic acid molecule, a chimeric nucleic acid molecule, and/or a recombinant nucleic acid construct or vector which comprise, consist, or essentially consist of a nucleic acid sequence that is at least 90% identical, at least 95% identical, at least 97% identical, at least 98% identical, at least 99% identical, or 100% identical to SEQ ID NO: 1. The present invention also provides an isolated nucleic acid molecule that is at least 90% identical, at least 95% identical, at least 97% identical, at least 98% identical, at least 99% identical, or 100% identical to SEQ ID NO: 1. The present invention also provides for a nucleic acid molecule, a chimeric nucleic acid molecule, and/or a recombinant nucleic acid construct or vector which comprise, consist, or consist essentially of SEQ ID NO: 1. The present invention also provides for a nucleic acid molecule, a chimeric nucleic acid molecule, and/or a recombinant nucleic acid construct or vector which comprise, consist, or consist essentially of a nucleic acid sequence that is at least 90% identical, at least 95% identical, at least 97% identical, at least 98% identical, at least 99% identical, or 100% identical to SEQ ID NO: 1.

In one embodiment, this chimeric nucleic acid molecule may comprise additional expression cassettes, transcriptional or translational regulatory elements, or prokaryotic origins of replication. In another embodiment, the chimeric nucleic acid molecule may be a recombinant nucleic acid construct, such as a binary vector or a vector suitable for expression in prokaryotes. The recombinant nucleic acid construct may be suitable for transient or stable expression in plants. In another embodiment, the invention encompasses SEQ ID NO: 1 or a nucleic acid molecule that is substantially identical to SEQ ID NO: 1 as either an isolated nucleic acid molecule or as part of a larger nucleic acid molecule.

The present invention also provides for use of a nucleic acid molecule of the invention as described herein, wherein expression of said nucleic acid molecule in a cell confers herbicide tolerance.

The present invention also provides for a transgenic host cell comprising a nucleic acid molecule of the invention as described herein. The transgenic host cell described above may be a bacterial cell or a plant cell. The transgenic bacterial cell may be an *Escherichia coli, Bacillus thuringiensis, Bacillus subtilis, Bacillus megaterium; Bacillus cereus, Agrobacterium* ssp. or a *Pseudomonas* ssp. cell. The transgenic plant cell may be found within a transgenic plant, plant part, plant tissue, or plant cell culture. The transgenic plant may be a monocotyledonous or dicotyledonous plant. The transgenic plant may be selected from the group comprising maize, sorghum, wheat, sunflower, tomato, crucifers, oat, turf grass, pasture grass, peppers, potato, cotton, rice, soybean, sugarcane, sugar beet, tobacco, barley, and oilseed rape.

The present invention also provides for a progeny of any generation of a transgenic plant, wherein said transgenic plant comprises a nucleic acid molecule of the invention as described herein. The present invention also provides for a transgenic seed, a cutting from a transgenic plant for the purposes of propagation, and for a transgenic propagule from said transgenic plant.

The present invention also provides for a method of producing an herbicide tolerant transgenic plant, comprising introducing a nucleic acid molecule of the invention as described herein into a plant thereby producing a transgenic plant, wherein the nucleic acid molecule is capable of expressing herbicide tolerance genes. In a preferred embodiment, the transgenic plant expresses herbicide tolerant genes in an amount that controls weeds.

The present invention also provides for a method of producing an herbicide tolerant plant, comprising the steps of (a) providing a nucleic acid molecule of the invention as described herein; (b) introducing into a plant, tissue culture, or a plant cell the nucleic acid molecule of step (a) to obtain a transformed plant, transformed tissue culture, or a transformed cell having herbicide tolerance; and (c) growing said transformed plant or regenerating a transformed plant from the transformed tissue culture or transformed plant cell, so a herbicide tolerant plant is produced. The present invention also provides for a method of producing transgenic seed from the transgenic plant described above, where the plant is cultured or grown under appropriate conditions to produce progeny seed which is transgenic.

The present invention also provides for a method of producing progeny of any generation of an herbicide tolerant fertile transgenic plant, comprising the steps of: (a) obtaining a herbicide tolerant fertile transgenic plant comprising a nucleic acid molecule of the invention as described herein; (b) collecting transgenic seed from said transgenic plant; (c) planting the collected transgenic seed; and (d) growing the progeny transgenic plants from said seed, wherein said progeny has enhanced herbicide tolerance relative to a non-transformed plant.

The present invention also provides for a method for producing a plant with herbicide tolerance, comprising the steps of sexually crossing a first parent plant with a second parent plant, wherein said first or second parent plant is a transgenic plant comprising a nucleic acid molecule of the invention as described herein. A first generation progeny plant that is a transgenic plant comprising a nucleic acid molecule of the invention as described herein is produced. The present invention also provides for a method for producing a plant with herbicide tolerance, comprising the steps of: (a) sexually crossing a first parent plant with a second parent plant, wherein said first or second parent plant is a transgenic plant comprising a nucleic acid molecule of the invention as described herein; (b) selecting a first generation progeny plant with herbicide tolerance; (c) selfing the first generation progeny plant, thereby producing a plurality of second generation progeny plants; and (d) selecting from the second generation progeny plants a plant with herbicide tolerance, wherein the second generation progeny plants comprise a nucleic acid molecule of the invention as described herein.

EXAMPLES

Example 1: Constructs Synthesized

Five binary vector constructs were constructed with differing combinations of transcriptional enhancers, promoters, translational enhancers, and terminators, and variants of these genetic elements, driving expression of the genes encoding ZmEPSPS and PAT. All promoters used are known to be strong constitutive promoters, and the addition of the transcriptional and translational enhancers were expected to result in transgenic plants with excellent levels of expression and herbicide tolerance. Table 1 shows the five constructs created, and lists the genetic elements with each gene of interest (GOI). Table 2 describes each of the genetic elements named in Table 1.

TABLE 1

Composition of Binary Constructs

| Construct ID | Transcriptional enhancer | Promoter | Translational enhancer | GOI | Terminator |
|---|---|---|---|---|---|
| 17869 | eFMV-03:e35S-05 | prAct1-07 | eTMV-02 | cZmEPSPSct-01 | t35S-08:tNOS-05-01 |
|  | eNOS-01 | prUbi1-18 |  | cPAT-03-02 | t35S-08:tNOS-05-01 |
| 18472 | eFMV-03:e35S-05:eNOS-01 | prCMP-08 | eTMV-02 | cZmEPSPSct-01 | tNOS-05-01 |
|  |  | pr35S-04 |  | cPAT-03-01 | tNOS-05-01 |

TABLE 1-continued

Composition of Binary Constructs

| Construct ID | Transcriptional enhancer | Promoter | Translational enhancer | GOI | Terminator |
|---|---|---|---|---|---|
| 18857 | eFMV-05:e35S-05 | prZmUbi158-02 | eTMV-03 | cZmEPSPSct-02 | tZmUbi158-02 |
|  |  | pr35S-19 |  | cPAT-09 | tNOS-05-01 |
| 18943 | eFMV-03:e35S-05:eNOS-01 | prCMP-08 | eTMV-02 | cZmEPSPSct-02 | tNOS-05-01 |
|  |  | pr35S-19 |  | cPAT-09 | tNOS-05-01 |
| 19119 | eFMV-06:e35S-11:eNOS-03 | prCMP-10 | eTMV-02 | cZmEPSPSct-02 | tNOS-05-01 |
|  |  | pr35S-19 |  | cPAT-09 | tNOS-05-01 |

TABLE 2

Description of Genetic Elements

| Element | Name | Description |
|---|---|---|
| promoter | prAct1-07 | Modified rice actin promoter. |
| promoter | prUbi1-18 | Modified maize ubiquitin promoter, similar to the maize polyubiquitin promoter NCBI accession number S944646.1; (Christensen et al. 1992, *PMB* 18: 675-689). |
| promoter | pr35S-04 | Modified promoter region of cauliflower mosaic virus (Odell et al. 1985, *Nature* 313: 810-812). |
| promoter | pr35S-19 | Modified promoter region of cauliflower mosaic virus (Odell et al. 1985, *Nature* 313: 810-812). Differs from pr35S-04 by 4 bp changes. |
| promoter | prCMP-08 | A modified version of Cestrum Yellow Leaf Curling Virus Promoter (Stavolone et al., 2003, *PMB* 53: 663-73) with a translational enhancing cis-element from Maize histone H3 gene. |
| promoter | prCMP-10 | Differs from prCMP-08 by 7 bp changes. |
| promoter | prZmUbi158-02 | Modified maize constitutive promoter based on the maize Ubiquitin ZmU29158-3 gene. It is similar to the maize polyubiquitin promoter (NCBI accession number S94466.1; Christensen et al. 1992, *PMB* 18: 675-689). |
| transcriptional enhancer | eNOS-01 | Modified NOS enhancer from *Agrobacterium tumefaciens* |
| transcriptional enhancer | eNOS-03 | Modified NOS enhancer from *Agrobacterium tumefaciens*. Differs from eNOS-01 by 2 bp changes. |
| transcriptional enhancer | eFMV-03 | Modified figwort mosaic virus enhancer region (similar to NCBI accession number X06166.1; Maiti et al. 1997, *Transgenic Res* 6: 143-156) |
| transcriptional enhancer | eFMV-05 | Modified figwort mosaic virus enhancer region (similar to NCBI accession number X06166.1; Maiti et al. 1997, *Transgenic Res* 6: 143-156). Differs from eFMV-03 by 2 bp changes. |
| transcriptional enhancer | eFMV-06 | Modified figwort mosaic virus enhancer region (similar to NCBI accession number X06166.1; Maiti et al. 1997, *Transgenic Res* 6: 143-156). Differs from eFMV-03 by 3 bp changes. |
| transcriptional enhancer | e35S-05 | Cauliflower mosaic virus 35S enhancer region which can activate heterologous core promoters (Ow et al. 1987, *PNAS* 84: 4870-4874.) |
| transcriptional enhancer | e35S-11 | Cauliflower mosaic virus 35S enhancer region which can activate heterologous core promoters (Ow et al. 1987, *PNAS* 84: 4870-4874.) Differs from e35S-05 by 2 bp changes. |
| translational enhancer | eTMV-02 | A modified version of the reverse orientation of the 5' non-coding leader sequence (called omega) from tobacco mosaic virus (Gallie et al. 1987, *Nucleic Acids Res* 15: 3257-3273). It functions as a translational enhancer in plants (Gallie. 2002, *Nucleic Acids Res* 15: 3257-3273). |
| translational enhancer | eTMV-03 | eTMV-02 fused to a maize-optimized Kozak sequence (TAAACC) |
| coding sequence | cPAT-03-01 | A modified version of the *S. viridochromogenes* strain Tü494 gene encoding the selectable marker PAT. The native coding sequence (Wohlleben et al. 1988, *Gene* 70: 25-37) was codon-optimized for enhanced expression. PAT confers resistance to herbicides containing glufosinate (phosphinothricin). |
| coding sequence | cPAT-03-02 | Differs from cPAT-03-02 by removal of two restriction enzyme sites. |
| coding sequence | cPAT-09 | The synthetic pat gene was obtained from AgrEvo, Germany (NCBI accession number DQ156557.1). The gene pat-09 encodes the same amino acid sequence as pat from AgrEvo, but several nucleotide changes were made to remove a cryptic splice site, a restriction site, and unintended ORFs. |

TABLE 2-continued

Description of Genetic Elements

| Element | Name | Description |
|---|---|---|
| coding sequence | cZmEPSPSct-01 | Sequence encoding the modified maize mEPSPS which confers tolerance to glyphosate (Lebrun et al. 2003, U.S. Pat. No. 6,566,587). Also comprises an N-terminal chloroplast transit peptide (CTP) sequences based on CTP sequences from *Helianthus annus* (sunflower) and maize, which directs the EPSPS protein to the chloroplast (Lebrun et al. 1996, U.S. Pat. No. 5,540,471) |
| coding sequence | cZmEPSPSct-02 | Differs from cZmEPSPSct-01 by 1 bp change |
| terminator | t35S-08 | Modified Cauliflower Mosaic Virus 35S terminator (Genbank V00141 J02048) |
| terminator | tNOS-05-01 | Terminator sequence from the NOS gene of *A. tumefaciens* (NCBI accession number V00087.1). Provides a polyadenylation site (Bevan et al. 1983, *Nucleic Acids Res* 11: 369-385). |
| terminator | tZmUbi158-02 | The terminator based on the maize Ubiquitin ZmU29158-3 gene. It is similar to the maize polyubiquitin terminator (NCBI accession number S94466.1; Christensen et al. 1992). The original Ubi158 terminator was altered by 1 bp to eliminate an unintended ORF. |

Example 2: Transformation Efficiency

Each of the five binary vector constructs was used to create maize transgenic events. Events were produced by *Agrobacterium*-mediated transformation of a proprietary maize line. Immature embryos were transformed essentially as described in Negrotto et al. (2000, *Plant Cell Reports* 19: 798-803). Using this method, genetic elements within the left and right border regions of the transformation plasmid were efficiently transferred and integrated into the genome of the plant cell, while genetic elements outside these border regions were not transferred.

The PAT gene was used as a selectable marker during the transformation process (Negrotto et al. 2000). The embryos producing embryogenic calli were transferred to a series of cell culture selection media containing bialaphos as selection agent and cultured for 10-11 weeks in total. The selection media contained 200 mg/ml timentin and/or 10 ml/l PPM (Plant Preservative Mix) to ensure that the *Agrobacterium* was cleared from the transformed tissue. Regenerated plants were transferred to the greenhouse for further propagation.

Table 3 shows the transformation efficiency for each construct. Transformation frequency is calculated as the percentage of transgenic events for a given construct with a given number of immature embryos used for the transformation. For example, if 100 immature maize embryos were initially transformed, and it was eventually determined that 5 of the events contained full or part of the T-DNA, the transformation frequency would be 5%.

TABLE 3

Transformation Efficiency

| Construct | Transformation Efficiency (%) |
|---|---|
| 17869 | 1.03 |
| 18472 | 4.15 |
| 18857 | 4.87 |
| 18943 | 6.03 |
| 19119 | 6.34 |

Surprisingly, one construct, 17869, had a very low transformation efficiency, which was neither predicted nor expected based on the composition of the binary construct.

Example 3: Gene Expression Determined by Quantitative Sandwich ELISA

EPSPS and PAT gene expression were determined by immunoassay, specifically by quantitative sandwich ELISA for the detection of PAT or for the detection of EPSPS. Protein extract samples were prepared from two ¼ inch maize leaf punches sampled into 96-well blocks, which were then macerated, clarified, and diluted in ELISA diluent (PBS containing 1% BSA, 0.05% Tween-20).

For the quantitative ELISA sandwich for the detection of EPSPS, one polyclonal antibody produced against the rice EPSPS protein and one monoclonal antibody produced against the soy EPSPS protein were used. Standards (160, 80, 40, 20, 10, 5, 2.5, and 0 ng/ml of purified mEPSPS protein) were prepared in ELISA diluent. Donkey anti-mouse conjugated to alkaline phosphatase (Jackson ImmunoResearch, West Grove, Pa.) and the substrate p-nitrophenyl phosphate (Surmodics) were used for detection and quantification. The absorbance was measured at 405 nm using a microplate reader (BioTek Powerwave XS2, Winooski, Vt.). The standard curve used a four-parameter curve fit to plot the concentrations versus the absorbance.

TABLE 4

Summary of EPSPS expression data

| Construct | #Events | Average EPSPS protein (ng/mg total protein) |
|---|---|---|
| 17869 | 33 | 84 |
| 18472 | 213 | 163 |
| 18857 | 382 | 2762 |
| 18943 | 586 | 61 |
| 19119 | 468 | 837 |

Surprisingly, the expression of ZmEPSPS protein was consistently lower in plants with the transgene from constructs 18472 and 18943, while the expression of ZmEPSPS protein from plants with the transgene from construct 18857 was significantly higher.

For PAT, the assay employed rabbit and goat polyclonal antibodies which have been produced against the PAT protein and affinity purified (IAP) against the PAT protein. Standards (32, 16, 8, 4, 2, 1, 0.5, and 0 ng/ml of purified PAT protein) were prepared in ELISA diluent. Donkey anti-goat conjugated to alkaline phosphatase and substrate p-nitrophenyl phosphate (Surmodics) were used for detection and quantification. The absorbance was measured at 405 nm using a microplate reader (BioTek Powerwave XS2, Winooski, Vt.). The standard curve used a four-parameter curve fit to plot the concentrations versus the absorbance.

TABLE 5

Summary of PAT expression data

| Construct | #Events | Average PAT protein (ng/mg total protein |
|---|---|---|
| 17869 | 33 | 179 |
| 18472 | 213 | 158 |
| 18857 | 382 | 59 |
| 18943 | 586 | 9 |
| 19119 | 468 | 8 |

Surprisingly, the expression of PAT protein was consistently lower in plants with the transgene from constructs 18943 and 19119, while the expression of PAT protein from plants with the transgene from construct 18472 or 17869 was significantly higher.

Example 4: Field Trial Efficacy

Field efficacy for glyphosate was tested. Field efficacy was evaluated using transgenic events of each construct. The table below shows the results of a field efficacy trial using glyphosate. For this trial, phytotoxicity of glyphosate on events was scored and issues regarding male sterility were determined. To pass the test, an event had to have tolerance to glyphosate comparable to the commercial maize event GA21 and have no issues with male fertility.

TABLE 6

Glyphosate Field Efficacy Trial

| Construct | # Events Tested | # Events passed | % Events passed |
|---|---|---|---|
| 17869 | 7 | 0 | 0 |
| 18472 | 50 | 2 | 4 |
| 18857 | 52 | 35 | 67 |
| 18943 | 15 | 0 | 0 |
| 19119 | 28 | ** | ** |

** Events from 19119 were not tested for male fertility issues because they had higher phytotoxicity compared to events from 18857.

Events from construct 18857 had the most events which passed the field efficacy trial. This is consistent with the high levels of ZmEPSPS protein expression that was detected by ELISA (Table 4). However, surprisingly, events from construct 19119 did not pass the field efficacy trial, despite having good ZmEPSPS protein expression as shown in Table 4. This suggests that the ZmEPSPS protein expression results cannot be predictive of performance in the field.

Table 6 clearly shows that the binary vector construct 18857 created the most transgenic events which could pass field efficacy trials, both for herbicide tolerance and for no issues with male fertility. This result was unexpected and unpredictable.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. A nucleic acid molecule comprising a nucleic acid sequence that is at least 90% identical to SEQ ID NO: 1, or a full complement thereof.

2. An isolated nucleic acid molecule comprising a nucleic acid sequence that is at least 95% identical SEQ ID NO: 1, or a complement thereof.

3. A chimeric nucleic acid molecule comprising the nucleic acid molecule of claim 1.

4. A recombinant nucleic acid vector comprising the nucleic acid molecule of claim 1.

5. A transgenic host cell comprising the nucleic acid molecule of claim 1.

6. A transgenic host cell according to claim 5, wherein said cell is a bacterial cell or a plant cell.

7. The host cell according to claim 6, wherein the bacterial cell is an *Escherichia coli, Bacillus thuringiensis, Bacillus subtilis, Bacillus megaterium, Bacillus cereus, Agrobacterium* ssp., and *Pseudomonas* ssp. cell.

8. A transgenic plant, plant part, plant tissue, or plant cell culture comprising the transgenic plant cell of claim 6.

9. The transgenic plant according to claim 8, wherein said plant is a monocot plant.

10. The transgenic plant according to claim 8, wherein said plant is a dicot plant.

11. A transgenic plant according to claim 8, wherein said plant is selected from the group consisting of maize, sorghum, wheat, sunflower, tomato, crucifers, oat, turf grass, pasture grass, peppers, potato, cotton, rice, soybean, sugarcane, sugar beet, tobacco, barley, and oilseed rape.

12. A progeny of any generation of the plant of claim 8, wherein the progeny comprises a nucleic acid sequence that is at least 90% identical to SEQ ID NO: 1, or a full complement thereof.

13. A propagule from any generation of the transgenic plant of claim 8, wherein the propagule comprises a nucleic acid sequence that is at least 90% identical to SEQ ID NO: 1, or a full complement thereof.

14. The propagule of claim 13, further defined as a seed or a cutting.

15. A method of producing a transgenic plant with herbicide tolerance, comprising introducing the nucleic acid molecule of claim 1 into a plant thereby producing the transgenic plant, wherein the nucleic acid molecule expresses effective amounts of protein to confer herbicide tolerance.

16. A method of producing a transgenic plant with herbicide tolerance, comprising the steps of:
   a) providing the nucleic acid molecule of claim 1;
   b) introducing into a plant, tissue culture, or a plant cell the nucleic acid molecule of step a) to obtain a transformed plant, transformed tissue culture, or a transformed cell having
   herbicide tolerance; and
   c) growing said transformed plant or regenerating a transformed plant from the transformed tissue culture or transformed plant cell, thereby producing the transgenic plant with herbicide tolerance.

17. A method of producing transgenic seed, comprising the steps of:
   a) obtaining the transgenic plant according to claim 8; and
   b) growing said plant under appropriate conditions to produce said transgenic seed.

18. A method of producing progeny of any generation of a fertile transgenic plant with herbicide tolerance, comprising the steps of:
   a) obtaining a fertile transgenic plant with herbicide tolerance, wherein said plant comprises the nucleic acid molecule of claim 1;
   b) collecting transgenic seed from said transgenic plant;
   c) planting the collected transgenic seed; and
   d) growing the progeny transgenic plants from said seed, wherein said progeny has herbicide tolerance relative to a, wherein said progeny comprises the nucleic acid molecule of claim 1.

19. A method for producing a transgenic plant with herbicide tolerance, comprising the steps of sexually crossing a first parent plant with a second parent plant, wherein said first or second parent plant is the transgenic plant of claim 8, to produce a first generation progeny plant that comprises a nucleic acid sequence that is at least 90% identical to SEQ ID NO: 1, or a complement thereof.

20. A method for producing a transgenic plant with herbicide tolerance, comprising the steps of:
   a) sexually crossing a first parent plant with a second parent plant, wherein said first or second parent plant is the transgenic plant of claim 8;
   b) selecting a first generation progeny plant with herbicide tolerance;
   c) selfing the first generation progeny plant, thereby producing a plurality of second generation progeny plants; and
   d) selecting from the second generation progeny plants a plant with herbicide tolerance,
wherein the second generation progeny plants comprise a nucleic acid sequence that is at least 90% identical to SEQ ID NO: 1, or a full complement thereof.

* * * * *